United States Patent
Khamatnurova et al.

(10) Patent No.: US 10,215,679 B2
(45) Date of Patent: Feb. 26, 2019

(54) THIN-LAYER CHROMATOGRAPHY FOR SCREENING OIL-FIELD SURFACTANTS

(71) Applicant: Halliburton Energy Services, Inc., Houston, TX (US)

(72) Inventors: Tatyana V. Khamatnurova, Houston, TX (US); Jeremy Holtsclaw, Kingwood, TX (US); Kristina Henkel Holan, Kingwood, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 156 days.

(21) Appl. No.: 15/220,801

(22) Filed: Jul. 27, 2016

(65) Prior Publication Data
US 2018/0031463 A1    Feb. 1, 2018

(51) Int. Cl.
*G01N 11/02*    (2006.01)
*G01N 30/90*    (2006.01)
*G01N 30/88*    (2006.01)

(52) U.S. Cl.
CPC ............. *G01N 11/02* (2013.01); *G01N 30/90* (2013.01); *G01N 2030/8854* (2013.01)

(58) Field of Classification Search
CPC .................................................... G01N 11/02
See application file for complete search history.

(56) References Cited

U.S. PATENT DOCUMENTS

| | | | | |
|---|---|---|---|---|
| 4,292,041 A | * | 9/1981 | Fullerton | G01N 30/94 210/658 |
| 5,824,214 A | * | 10/1998 | Paul | C10G 15/08 208/107 |
| 8,589,130 B2 | * | 11/2013 | Stukan | E21B 43/16 703/6 |
| 2012/0285231 A1 | * | 11/2012 | Rickman | E21B 43/16 73/152.18 |

(Continued)

OTHER PUBLICATIONS

Thin-Layer Chromatography, https://web.archive.org/web/20030611004838/http://courses.chem.psu.edu:80/chem36/Experiments/PDF's_for_techniques/TLC.pdf, Jun. 11, 2003 (Internet Archive—Wayback Machine), pp. 93-103.*

(Continued)

*Primary Examiner* — Daniel S Larkin
(74) *Attorney, Agent, or Firm* — Kilpatrick Townsend & Stockton LLP

(57) ABSTRACT

A thin-layer chromatography device can be used to determine or select a surfactant solution for use during hydrocarbon-fluid production operations. The thin-layer chromatography device can include a chamber that can receive a surfactant solution that includes a surfactant and a fluid. The thin-layer chromatography device can also include a substrate that can be coated with a layer of adsorbent material to form a thin-layer substrate and a hydrocarbon fluid can be disposed on the thin-layer substrate. The thin-layer substrate, along with the hydrocarbon fluid, can be positioned within the chamber to determine a mobility index of the hydrocarbon fluid when the hydrocarbon fluid contacts the (Continued)

surfactant solution. The mobility index can indicate an eluting capability of the surfactant solution with respect to the hydrocarbon fluid and can be used to select the surfactant solution to be injected into a wellbore that includes the hydrocarbon fluid to enhance hydrocarbon-fluid production operations.

19 Claims, 6 Drawing Sheets

(56) References Cited

U.S. PATENT DOCUMENTS

2013/0067999 A1* 3/2013 Xu .................. G01N 13/02
73/64.51

OTHER PUBLICATIONS

Bhawani, S.A. et al., "Surfactant Modified/Mediated Thin-Layer Chromatographic Systems for the Analysis of Amino Acids", Journel of Analytical Methods in Chemistry, 2013, pp. 1-8.*

* cited by examiner

THIN-LAYER CHROMATOGRAPHY FOR SCREENING OIL-FIELD SURFACTANTS

TECHNICAL FIELD

The present disclosure relates generally to wellbore drilling. More specifically, but not by way of limitation, this disclosure relates to a thin-layer chromatography device for screening oil-field surfactants.

BACKGROUND

A well system (e.g., oil or gas wells for extracting fluids from a subterranean formation) can include a production well and an injection well. During production operations, various equipment, components, methods, or techniques can be used to displace and recover hydrocarbon fluid (e.g., oil) from within the production well. For example, a solution can be injected into the injection well to increase a mobility of the hydrocarbon fluid and sweep the hydrocarbon fluid from within the production well to enhance hydrocarbon recovery.

DETAILED DESCRIPTION

Figure 1:
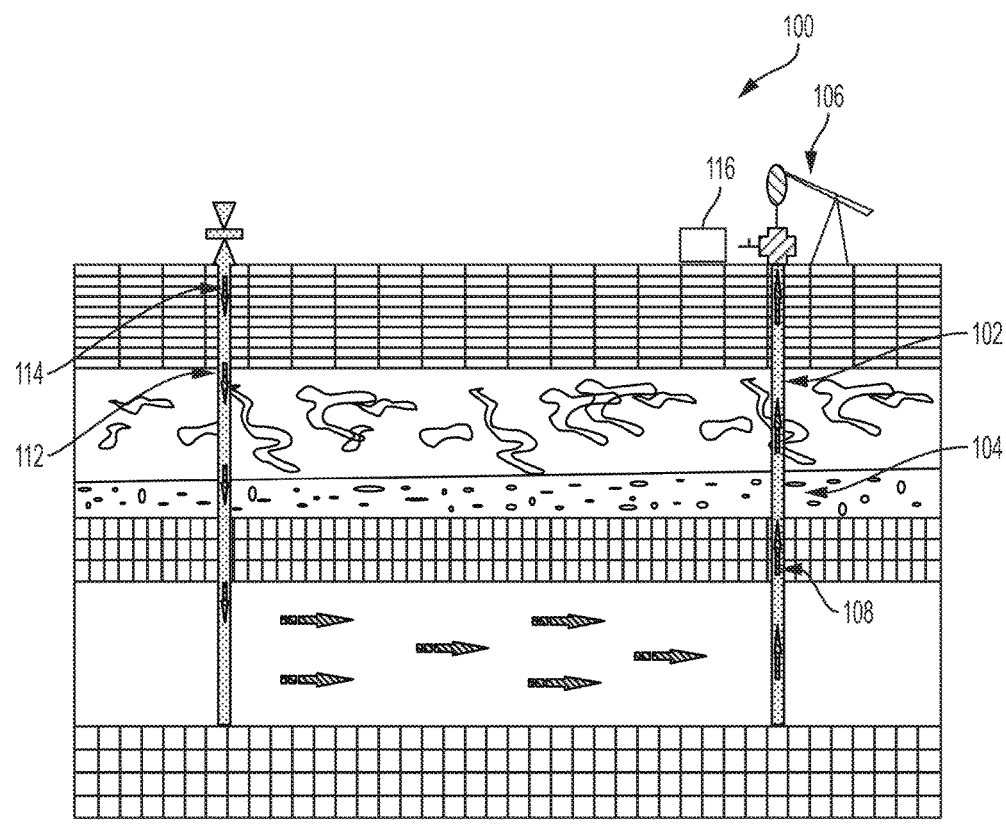
FIG. 1 is a schematic diagram of a well system that can include a thin-layer chromatography device for screening oil-field surfactants, according to one example of the present disclosure.

Certain aspects and features of the present disclosure are directed to a thin-layer chromatography device for screening oil-field surfactants. The thin-layer chromatography device can include a sample chamber and a stationary phase substrate (e.g., a plastic or metal substrate). The substrate can be coated with a layer of adsorbent material to form a thin-layer substrate. The adsorbent material can be any material that can adhere to atoms, ions, or molecules from fluid, liquid, or dissolved solids. In some examples, an amount of a hydrocarbon fluid sample can be disposed on the thin-layer substrate and may be adsorbed or bound to the adsorbent material. A surfactant solution can be disposed within the sample chamber and the thin-layer substrate, along with the hydrocarbon fluid sample, can be inserted into the sample chamber and into the surfactant solution. A mobility index associated with the hydrocarbon fluid sample can be determined after the thin-layer substrate is inserted to the surfactant solution and the surfactant solution can be selected to be injected into a wellbore based at least in part on the mobility index of the hydrocarbon fluid sample.

During operations for producing hydrocarbon fluid, a surfactant solution can be injected into a wellbore to increase the mobility of hydrocarbon fluids in the wellbore and enhance hydrocarbon fluid recovery. The surfactant of the surfactant solution can reduce a surface tension between hydrocarbon fluids in the wellbore and solids in the wellbore to displace the hydrocarbon fluids from within the wellbore and up toward a surface of the wellbore. In some examples, the thin-layer chromatography device can be used to determine a type of surfactant solution to be injected into the wellbore during the operations.

For example, the thin-layer substrate of the chromatography device, along with a hydrocarbon fluid sample disposed on the thin-layer substrate, can be positioned within the sample chamber that includes a surfactant solution. The surfactant solution can flow past or across the thin-layer substrate, which can cause the hydrocarbon fluid sample to contact the surfactant solution. In some examples, the surfactant in the surfactant solution can weaken a bond between the hydrocarbon fluid sample and an adsorbent material disposed on the thin-layer substrate or reduce a surface tension between the hydrocarbon fluid sample and the adsorbent material. Reducing the surface tension or weakening the bond between the hydrocarbon fluid sample and the adsorbent material can affect a mobility index of the hydrocarbon fluid sample. The mobility index of the hydrocarbon fluid sample can be based on a displacement or a distance traveled by the hydrocarbon fluid sample along the thin-layer substrate (e.g., a distance between a first position of the hydrocarbon fluid sample on the thin-layer substrate and a second position of the hydrocarbon fluid sample on the thin-layer substrate). For example, reducing the surface tension or weakening the bond between the hydrocarbon fluid and the adsorbent material can allow the hydrocarbon fluid to travel a long distance along the thin-layer substrate, which can increase the mobility index of the hydrocarbon fluid.

As another example, the mobility index of the hydrocarbon fluid sample may be based on a retention factor of the hydrocarbon fluid sample. The retention factor can be based on the distance traveled by the hydrocarbon fluid sample along the thin-layer substrate and a distance traveled by the surfactant solution along the thin-layer substrate (e.g., a length of the thin-layer substrate covered by the surfactant solution when the thin-layer substrate is positioned within the sample chamber). As still another example, the mobility index of the hydrocarbon fluid sample may be based on a rate at which the hydrocarbon fluid sample travels the distance along the thin-layer substrate (e.g., a velocity at which the hydrocarbon fluid sample travels the distance between a first position on the thin-layer substrate and a second position on the thin-layer substrate).

The mobility index of the hydrocarbon fluid sample can correspond to an eluting capability of the surfactant solution, which may indicate an ability of the surfactant solution to displace or separate the hydrocarbon fluid sample from the adsorbent material. In some examples, a surfactant solution to be injected into a wellbore during production operations can be selected based on the mobility index of the hydrocarbon fluid sample. For example, the hydrocarbon fluid sample that is disposed on the thin-layer substrate can be a hydrocarbon fluid from within the wellbore. The surfactant solution can be selected for the wellbore to enhance production operations if the mobility index of the hydrocarbon fluid sample is above a mobility index threshold.

These illustrative examples are given to introduce the reader to the general subject matter discussed here and are not intended to limit the scope of the disclosed concepts. The following sections describe various additional features and examples with reference to the drawings in which like numerals indicate like elements, and directional descriptions are used to describe the illustrative examples but, like the illustrative examples, should not be used to limit the present disclosure.

FIG. 1 is a schematic diagram of a well system 100 that can include a thin-layer chromatography device 116 for screening oil-field surfactants, according to one example of the present disclosure.

In this example, the well system 100 can include a production well 102 and an injection well 112. The well system 100 can be an oil or gas well system for extracting fluids from a hydrocarbon bearing formation 104. A pump 106 (e.g., a beam pump or a pump jack) can be used to produce hydrocarbon fluid 108 (e.g., gas or oil) from the production well 102.

The injection well 112 can be a well that is associated with, or positioned proximate to, the production well 102. A surfactant solution 114 can be injected into the injection well 112 for surfactant flooding the production well 102. In some examples, the surfactant solution 114 may sweep hydrocarbon fluid 108 toward the production well 102 as the surfactant solution 114 flows from the injection well 112 toward the production well 102.

The surfactant solution 114 can include a fluid. Examples of the fluid include, but are not limited to, produced water, brine, or fracturing fluid. Produced water can be water that is produced from a wellbore and is not a treatment fluid. Brine can be a solution of salt in water or water containing more dissolved inorganic salt than sea. Fracturing fluid can include water, a proppant (e.g., sand, sintered bauxite, or other particles), and a nonaqueous fluid (e.g., a gels, friction reducers, crosslinkers, breakers, surfactants, etc.).

The surfactant solution 114 can also include a surfactant. The surfactant can be any compound that can reduce a surface tension of a mixture. For example, the surfactant can reduce a surface tension between two or more liquids or reduce a surface tension between a liquid and a solid. As an example, the surfactant can reduce the surface tension between hydrocarbon fluid 108 and another fluid in the production well 102. As another example, the surfactant can reduce the surface tension between hydrocarbon fluid 108 and one or more solids in the production well 102 (e.g., formation cuttings, rocks, particles, etc.).

In some examples, the surfactant in the surfactant solution 114 can improve recovery of hydrocarbon fluid 108 from within the production well 102. For example, the surfactant in the surfactant solution 114 can alter a wettability of the production well 102 (e.g., a preference of a solid in the production well 102 to contact a liquid or gas, such as, for example, hydrocarbon fluid 108 in the production well 102) to improve recovery of hydrocarbon fluid 108 from within the production well 102. In some examples, the surfactant in the surfactant solution 114 can improve the recovery of hydrocarbon fluid 108 by increasing a mobility of hydrocarbon fluid 108 in the production well 102. For example, the surfactant in the surfactant solution 114 can displace the hydrocarbon fluid 108 from within the production well 102 and up toward a surface of the production well 102.

In some examples, a type of surfactant solution 114 (e.g., a type of surfactant or a type of fluid in the surfactant solution 114) that can be injected into the injection well 112 to recover hydrocarbon fluid 108 can be determined or selected based on various factors such as, for example, a property of the production well 102 or a characteristic of the surfactant solution 114. An example of a property of the production well 102 includes, but is not limited to, a type of hydrocarbon fluid 108 or other fluid in the production well 102. An example of a characteristic of the surfactant solution 114, includes, but is not limited to, an eluting capability of the surfactant solution 114. The eluting capability of the surfactant solution 114 can be an ability of the surfactant solution 114 to displace or separate the hydrocarbon fluid 108 from fluids or solids in the production well 102.

The thin-layer chromatography device 116 can be a device for separating components (e.g., solutes) of a mixture or composition by passing the mixture or composition through a medium (e.g., a liquid or gas) in which the components move at different rates. The thin-layer chromatography device 116 can be positioned proximate to the production well 102. In another example, the thin-layer chromatography device 116 can be positioned at a remote location (e.g., an offsite laboratory).

The thin-layer chromatography device 116 can be used to determine a type of surfactant solution 114 to be injected into the injection well 112. As an example, the thin-layer chromatography device 116 can be used to determine a mobility index associated with one or more hydrocarbon fluid samples (e.g., a sample of the hydrocarbon fluid 108) when the hydrocarbon fluid sample contact the surfactant solution 114, which can indicate an eluting capability of a surfactant solution 114 with regard to the hydrocarbon fluid samples. In some examples, the type of surfactant solution 114 that can be injected into the injection well 112 may be selected or determined based at least in part on the mobility index.

Although a single thin-layer chromatography device 116 is shown in FIG. 1, some embodiments may use multiple thin-layer chromatography devices for determining a type of surfactant or a type of fluid to be included in the surfactant solution 114.

Figure 2:
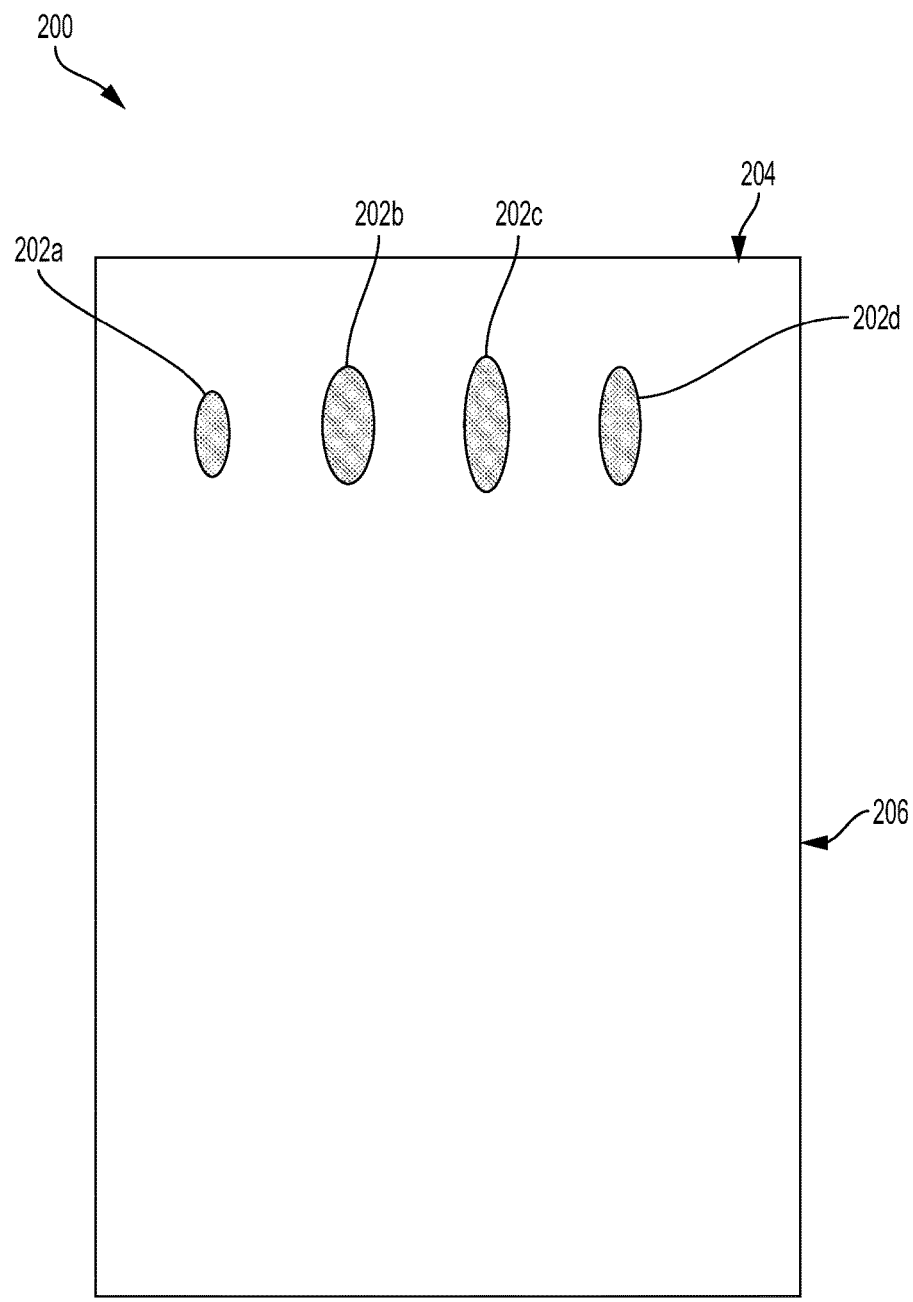
FIG. 2 is a perspective view of a thin-layer substrate of a thin-layer chromatography device for screening oil-field surfactants, according to one example of the present disclosure.

FIG. 2 is a perspective view of a thin-layer substrate 200 of the thin-layer chromatography device 116 for screening oil-field surfactants, according to one example of the present disclosure. The thin-layer substrate 200 can be any substrate (e.g., any material on which a process or reaction may occur). Examples of the thin-layer substrate 200 include, but are a not limited to, glass, plastic, aluminum foil, and quartz.

The thin-layer substrate 200 can include an adsorbent material (e.g., a material that can adhere to atoms, ions, or molecules from gas, liquid, or dissolved solid). For example, a layer of the adsorbent material can be applied (e.g., coated or otherwise disposed) on a side or surface of the thin-layer substrate 200. Examples of the adsorbent material include, but are not limited to, silica, alumina, cellulose, sand, and formation material. Formation material can include rocks or other particles from within a formation (e.g., the formation 104 of FIG. 1). In some examples, the adsorbent material can be an adsorbent material collected from a wellbore (e.g., from within the production well 102 of FIG. 1)

In some examples, an amount of a hydrocarbon fluid sample 202a-d (e.g., a sample of the hydrocarbon fluid 108 of FIG. 1 or other hydrocarbon fluid) can be applied or otherwise disposed on a side or surface of the thin-layer substrate 200. Each hydrocarbon fluid sample 202a-d can be any type of hydrocarbon fluid and can be of any amount. In some examples, each hydrocarbon fluid sample 202a-d can be a different type of hydrocarbon fluid. In some examples, the hydrocarbon fluid samples 202a-d can be applied on the same side or surface of the thin-layer substrate 200 as the adsorbent material on the thin-layer substrate 200. In some examples, the hydrocarbon fluid samples 202a-d can be applied at a first position on the thin-layer substrate 200. For example, in the example depicted in FIG. 2, the thin-layer substrate 200 can have a first end 204 and a second end 206 and the hydrocarbon fluid samples 202a-d can be deposited at a first position near the first end 204 of the thin-layer substrate 200.

A thin-layer chromatography device (e.g., the thin-layer chromatography device 116 of FIG. 1) can include the thin-layer substrate 200 and a sample chamber. For example, FIG. 3 is a perspective view of a thin-layer chromatography device 116 for screening oil-field surfactants, according to one example of the present disclosure.

Figure 3:
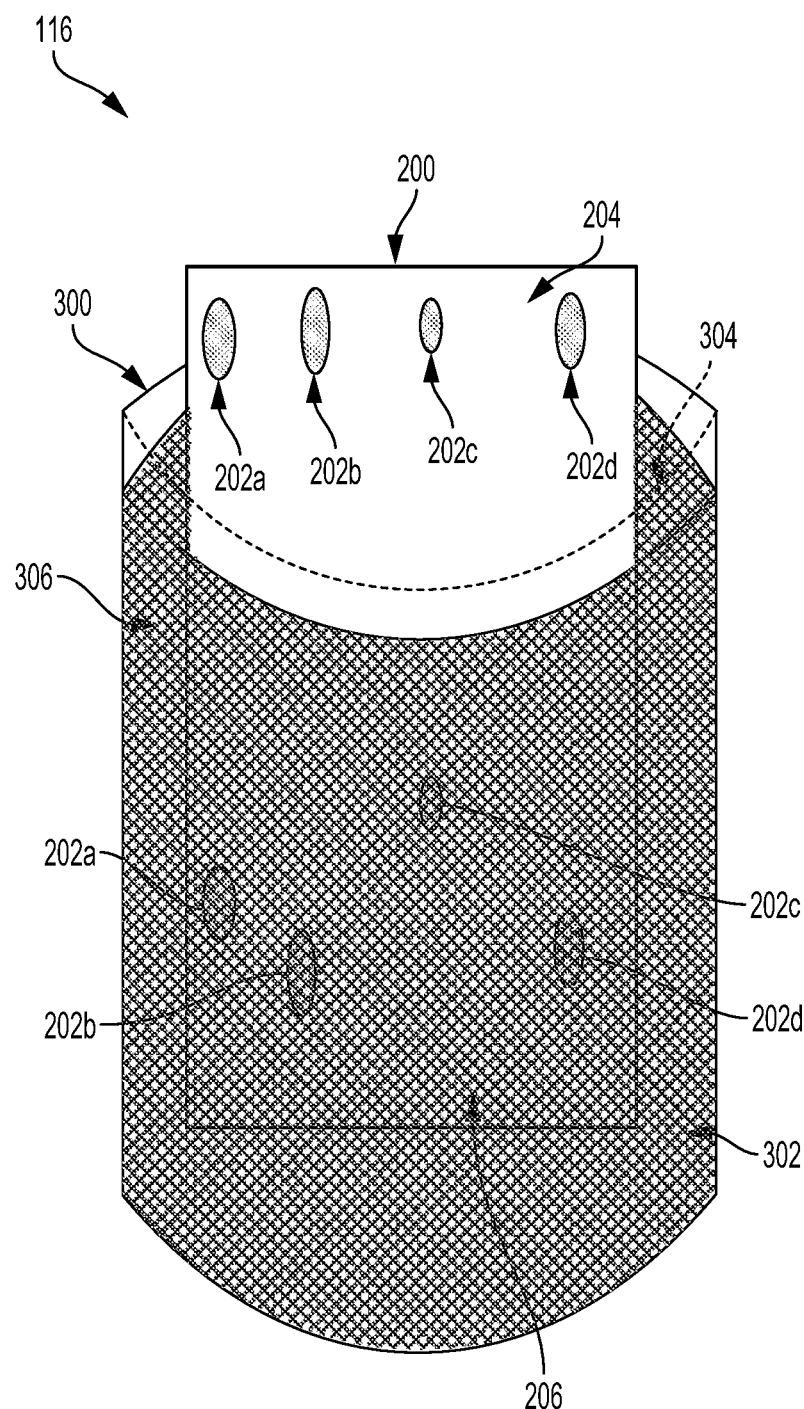
FIG. 3 is a perspective view of a thin-layer chromatography device for screening oil-field surfactants, according to one example of the present disclosure.

In the example depicted in FIG. 3, the thin-layer chromatography device 116 can include a sample chamber 300 and a thin-layer substrate 200 for determining a type of a surfactant solution 302 that can be used to recover hydrocarbon fluid from within a production well. For example, the thin-layer chromatography device 116 can be used to determine a type of surfactant or a type of fluid to be included in the surfactant solution 302.

The sample chamber 300 can be any chamber or passage. In some examples, the sample chamber 300 can allow surfactant solution 302 to flow in or within the sample chamber 300. For example, the sample chamber 300 can include an opening 304 through which the surfactant solution 302 can enter the sample chamber 300. The sample chamber 300 can also include a channel 306 for allowing the surfactant solution 302 to circulate or flow within the sample chamber 300.

In some examples, the thin-layer substrate 200, along with the hydrocarbon fluid samples 202a-d, can be positioned within (e.g., inserted into) the sample chamber 300. Positioning the thin-layer substrate 200, along with the hydrocarbon fluid samples 202a-d, within the sample chamber 300 can allow the surfactant solution 302 to flow across the thin-layer substrate 200 (e.g., along a length of the thin-layer substrate 200), which can cause the hydrocarbon fluid samples 202a-d to contact the surfactant solution 302 or interact with the surfactant solution 302.

The surfactant in the surfactant solution 302 may reduce a surface tension between the adsorbent material on the thin-layer substrate 200 and the hydrocarbon fluid samples 202a-d or weaken a bond between the adsorbent material and the hydrocarbon fluid samples 202a-d as the surfactant solution 302 contacts the hydrocarbon fluid samples 202a-d. Reducing the surface tension or weakening the bond between the adsorbent material and the hydrocarbon fluid samples 202a-d can affect a mobility of the hydrocarbon fluid samples 202a-d along the thin-layer substrate 200. For example, reducing the surface tension or weakening the bond between the adsorbent material and the hydrocarbon fluid samples 202a-d can allow each hydrocarbon fluid sample 202a-d to travel or flow from a first position on the thin-layer substrate 200 to a second position on the thin-layer substrate 200. In the example depicted in FIG. 3, each hydrocarbon fluid sample 202a-d can travel from a first position near the first end 204 of the thin-layer substrate 200 to a second position distal from the first end 204 (e.g., to a second position near the second end 206 of the thin-layer substrate 200).

A mobility index associated with each hydrocarbon fluid sample 202a-d can be determined based on a distance traveled by each hydrocarbon fluid sample 202a-d along the thin-layer substrate 200 (e.g., a distance between a first position of each hydrocarbon fluid sample 202a-d and a second position of each hydrocarbon fluid sample 202a-d).

Figure 4:
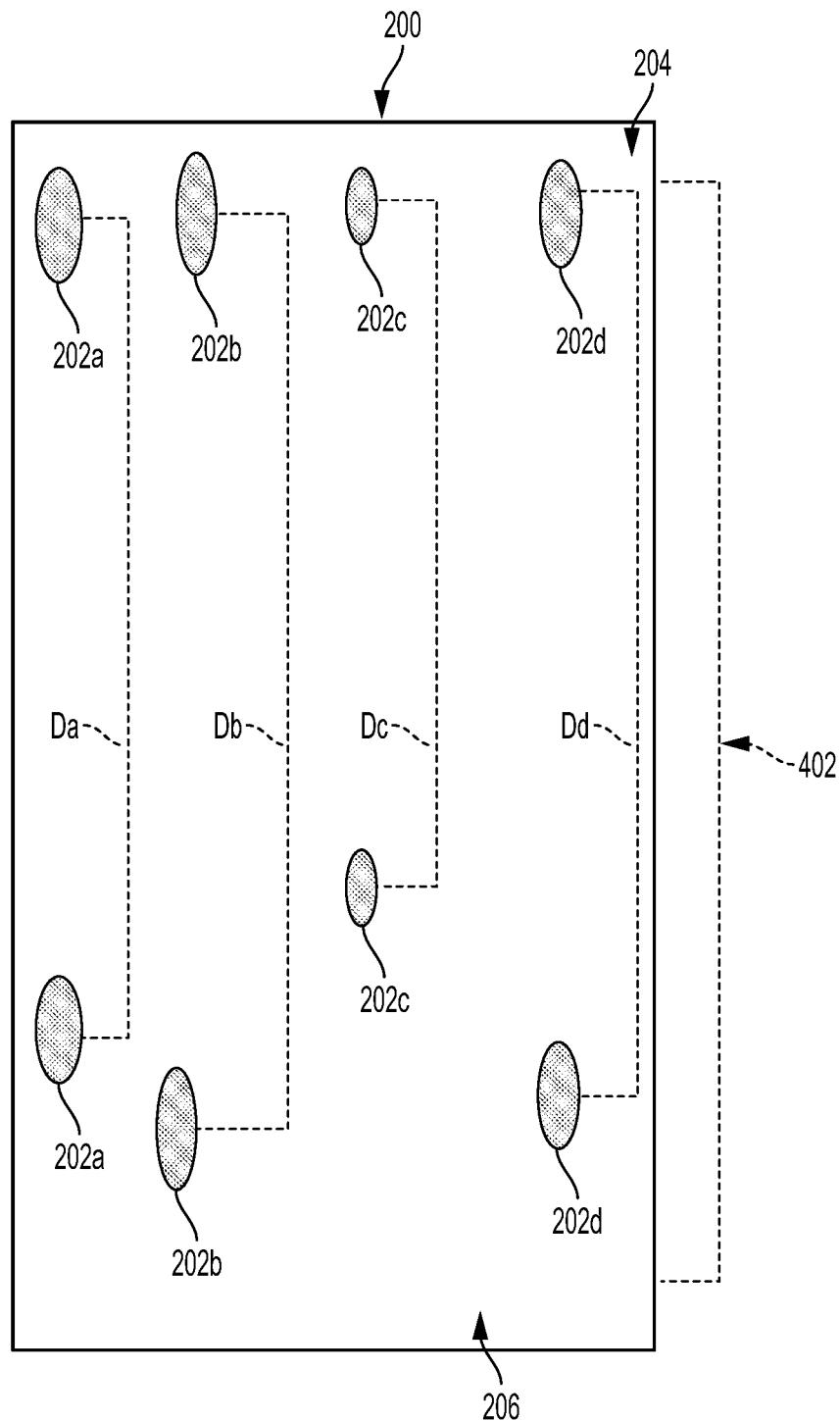
FIG. 4 is a perspective view of the thin-layer substrate of FIG. 2 showing a distance traveled by hydrocarbon fluid samples along the thin-layer substrate, according to one example of the present disclosure.

FIG. 4 is a perspective view of the thin-layer substrate 200 of FIG. 2 showing a distance traveled by hydrocarbon fluid samples 202a-d along the thin-layer substrate 200, according to one example of the present disclosure. The thin-layer substrate 200, along with the hydrocarbon fluid samples 202a-d, can be positioned within a sample chamber (e.g., the sample chamber 300 of FIG. 3) and subsequently removed from the sample chamber.

In this example, a surfactant solution (e.g., the surfactant solution 302 of FIG. 3) can flow across the thin-layer substrate 200 and cover or travel a length 402 of the thin-layer substrate 200 when the thin-layer substrate 200 is positioned within the sample chamber. The surfactant solution may also contact the hydrocarbon fluid samples 202a-d as the surfactant solution flows across the thin-layer substrate 200. In some examples, contact between the surfactant solution and the hydrocarbon fluid samples 202a-d can cause each hydrocarbon fluid sample 202a-d to travel or flow from a first position on the thin-layer substrate 200 to a second position on the thin-layer substrate 200.

For example, the thin-layer substrate 200 has a first end 204 and a second end 206. The hydrocarbon fluid samples 202a-d can be deposited at a first position near the first end 204 of the thin-layer substrate 200 and each hydrocarbon fluid sample 202a-d can travel or flow from the first position to a second position on the thin-layer substrate 200. For example, as depicted in FIG. 4, each hydrocarbon fluid sample 202a-d can travel from a first position near the first end 204 of the thin-layer substrate 200 to a second position distal from the first end 204 (e.g., toward the second end 206 of the thin-layer substrate 200). Each hydrocarbon fluid sample 202a-d can travel a respective distance $D_{a-d}$, which represents a distance between a respective first position and second position traveled by each hydrocarbon fluid sample 202a-d.

In some examples, a mobility index associated with each hydrocarbon fluid sample 202a-d can be determined based at least in part on the respective distance $D_{a-d}$ traveled by each hydrocarbon fluid sample 202a-d. For example, the mobility index associated with each hydrocarbon fluid sample 202a-d can be based on a retention factor of each hydrocarbon fluid sample 202a-d. The retention factor associated with each hydrocarbon fluid sample 202a-d can be a ratio between a distance $D_{a-d}$ traveled by each hydrocarbon fluid sample 202a-d and the length 402 of the thin-layer substrate 200 traveled by the surfactant solution. As an example, a retention factor associated with hydrocarbon fluid sample 202a can be a ratio between the distance $D_a$ and the length 402 traveled by the surfactant solution.

In another example, the mobility index associated with each hydrocarbon fluid sample 202a-d can be determined based on a rate (e.g., a velocity) at which each hydrocarbon fluid sample 202a-d travels a respective distance $D_{a-d}$. For example, a retention factor associated with the hydrocarbon fluid sample 202b can correspond to a velocity at which the hydrocarbon fluid sample 202b travels the distance $D_b$.

Returning to FIG. 3, as described above, the surfactant solution 302 can reduce the surface tension or weaken the bond between the adsorbent material on the thin-layer substrate 200 and the hydrocarbon fluid samples 202a-d, which may affect a mobility index of the hydrocarbon fluid samples 202a-d.

As an example, when the surfactant in the surfactant solution 302 contacts the hydrocarbon fluid sample 202a, the surfactant can reduce the surface tension between the adsorbent material and the hydrocarbon fluid sample 202a, which can increase a distance traveled by the hydrocarbon fluid sample 202a (e.g., increase the distance $D_a$ between the first position of the hydrocarbon fluid sample 202a on the thin-layer substrate 200 and the second position of the hydrocarbon fluid sample 202a on the thin-layer substrate 200 in FIG. 4). As another example, when the surfactant in the surfactant solution 302 contacts the hydrocarbon fluid sample 202a, the surfactant can reduce the surface tension between the adsorbent material and the hydrocarbon fluid sample 202a, which can increase a rate at which the hydrocarbon fluid sample 202a travels from a first position on the thin-layer substrate 200 to a second position on the thin-layer substrate 200 (e.g., increase a velocity at which the hydrocarbon fluid sample 202a travels distance $D_a$).

A mobility index of a hydrocarbon fluid sample 202a-d when the hydrocarbon fluid sample 202a-d contacts the surfactant solution 302 or an impact of the surfactant in the surfactant solution 302 on a mobility index of each hydrocarbon fluid sample 202a-d can depend on various factors such as, for example, a type of the hydrocarbon fluid sample 202a-d, a type of the adsorbent material on the thin-layer substrate 200, a type of the surfactant in the surfactant solution, and a type of the fluid in the surfactant solution.

In some examples, a mobility index of each hydrocarbon fluid sample 202a-d when the hydrocarbon fluid sample 202a-d contacts the surfactant solution 302 or an effect of the surfactant solution 302 on the mobility index of each hydrocarbon fluid sample 202a-d can indicate an eluting capability of the surfactant solution 302 with respect to each hydrocarbon fluid sample 202a-d. The eluting capability of the surfactant solution 302, with respect to each hydrocarbon fluid sample 202a-d, can represent an ability of the surfactant solution 302 to displace or separate each hydrocarbon fluid sample 202a-d from the adsorbent material on the thin-layer substrate 200 (e.g., an ability of the surfactant solution to reduce a surface tension between each hydrocarbon fluid sample 202a-d and the adsorbent material or weaken a bond between each hydrocarbon fluid sample 202a-d and the adsorbent material).

In some examples, surfactant solution 302 to be injected into an injection well during production operations can be selected or determined based at least in part on a mobility index of a hydrocarbon fluid sample 202a-d. For example, a production well associated with the injection well can include one or more hydrocarbon fluid samples 202a-d. The surfactant solution 302 can be selected to be injected into the injection well if the mobility index of one or more hydrocarbon fluid samples 202a-d is above a mobility index threshold. As an example, the production well can include hydrocarbon fluid sample 202a that has a high mobility index (e.g., a mobility index above the mobility index threshold) when the hydrocarbon fluid sample 202a contacts the surfactant solution 302. The surfactant solution 302 can be selected to be injected into the injection well positioned proximate to the production well to increase a mobility of hydrocarbon fluid sample 202a and sweep the hydrocarbon fluid sample 202a from within the production well, which can enhance hydrocarbon fluid recovery (e.g., by displacing hydrocarbon fluid sample 202a from within the production well toward the surface of the production well).

A surfactant solution 302 can be selected to be injected into an injection well based on a comparison of the mobility indices associated with the hydrocarbon fluid samples 202a-d. For example, the mobility index associated with hydrocarbon fluid sample 202b may be greater than the mobility index associated with the hydrocarbon fluid sample 202a when the hydrocarbon fluid samples 202a-d contact the surfactant solution 302. Based on the comparison, the surfactant solution 302 can be selected to be injected into the injection well positioned proximate to a production well that includes hydrocarbon fluid sample 202b to increase a mobility of hydrocarbon fluid sample 202b and sweep the hydrocarbon fluid sample 202b from within the production well, which can enhance hydrocarbon fluid recovery (e.g., by displacing hydrocarbon fluid sample 202b from within the production well toward the surface of the production well).

In another example, the adsorbent material disposed on the thin-layer substrate 200 can be collected from within a production well as well cuttings. The surfactant solution 302 can be selected to be injected into an injection well if the mobility index of one or more hydrocarbon fluid samples 202a-d is above the mobility index threshold. As an example, the production well can include hydrocarbon fluid sample 202b and formation material disposed on the thin-layer substrate 200 can be from within the production well. The hydrocarbon fluid sample 202b can have a high mobility index (e.g., a mobility index above the mobility index threshold) when the hydrocarbon fluid sample 202b contacts the surfactant solution 302 and the surfactant solution 302 can be selected to be injected into the injection well to increase a mobility of hydrocarbon fluid sample 202b and sweep the hydrocarbon fluid sample 202b from within the production well to enhance hydrocarbon fluid recovery.

In this manner, the thin-layer chromatography device 116 can be used to select a particular type of surfactant solution, from among a plurality of surfactant solutions, for a production well containing a particular type of hydrocarbon fluid or a particular type of adsorbent material based on a mobility index associated with the hydrocarbon fluid when the hydrocarbon fluid contacts the surfactant solution.

Figure 5:
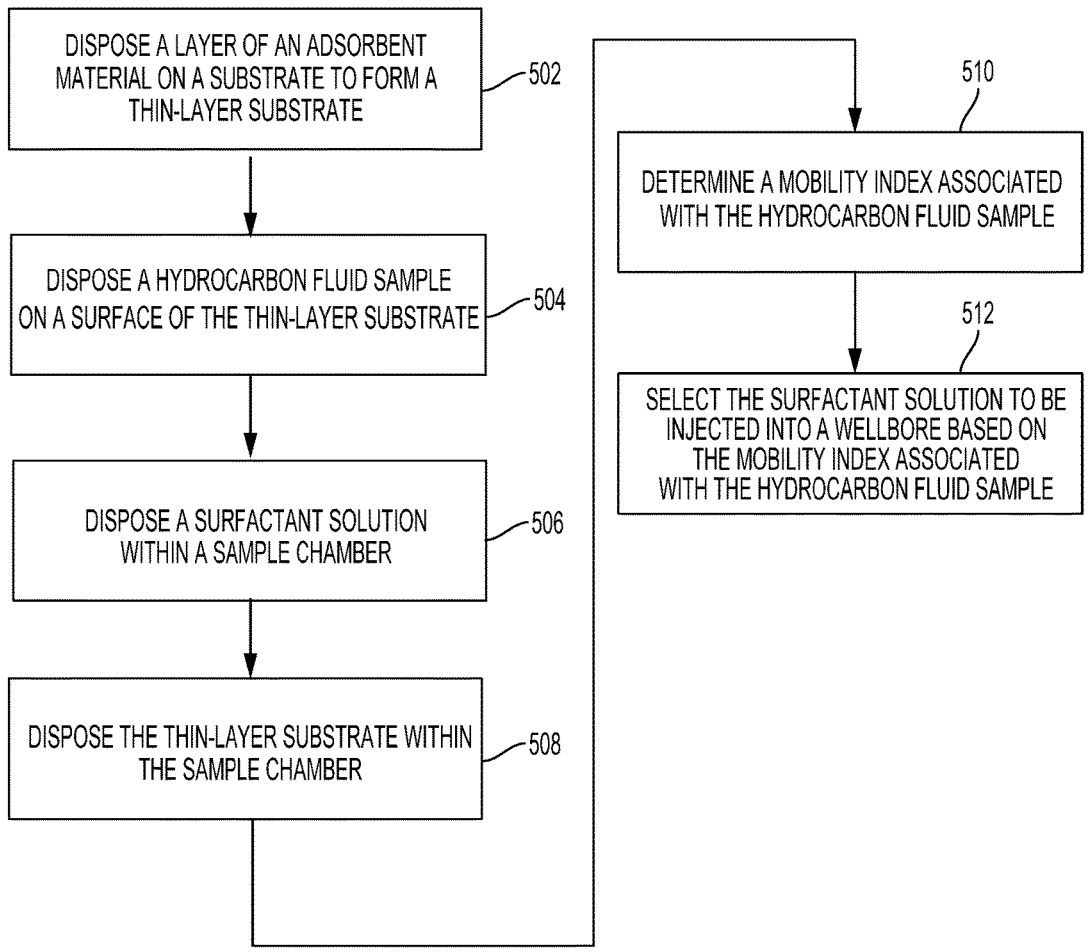
FIG. 5 is a flow chart depicting a process for screening oil-field surfactants using a thin-layer chromatography device, according to one example of the present disclosure.

FIG. 5 is a flow chart depicting a process for screening oil-field surfactants using a thin-layer chromatography device, according to one example of the present disclosure. The method of FIG. 5 will be described with respect to the example thin-layer chromatography device depicted in FIG. 1-4; however, the method is not limited to such examples. Rather, the method may be performed with any suitable thin-layer chromatography device according to this disclosure.

In block 502, a layer of an adsorbent material is disposed on a substrate to form a thin-layer substrate 200. The substrate can be any material on which a process or reaction may occur including, for example, glass, plastic, aluminum foil, and quartz. The adsorbent material can be any material that can adhere to atoms, ions, or molecules from gas, liquid, or dissolved solid. Examples of the adsorbent material include, but are not limited to, silica, alumina, cellulose, sand, or formation material (e.g., rocks or other particles from within a formation of a wellbore). In some examples, the adsorbent material can be collected from within a production well. The layer of the adsorbent material can be disposed on the substrate via any suitable method or technique. For example, the layer of the adsorbent material can be applied (e.g., coated or otherwise disposed) on a side or surface of the substrate. In some examples, the adsorbent material can be treated with fracturing fluid or formation water prior to being disposed on the substrate. Formation water can include water that occurs within the pores of a rock.

In block 504, a hydrocarbon fluid sample 202a (e.g., oil) is disposed on a surface of the thin-layer substrate 200 via any suitable method or technique, such as, for example, by applying or otherwise disposing the hydrocarbon fluid sample 202a on a side or surface of the thin-layer substrate 200. In some examples, the hydrocarbon fluid sample 202a can be disposed on the same side or surface of the thin-layer substrate 200 as the adsorbent material (e.g., in block 504). The hydrocarbon fluid sample 202a can be any type of hydrocarbon fluid and any amount of the hydrocarbon fluid sample 202a can be disposed on the surface of the thin-layer substrate 200.

In block 506, a surfactant solution 302 is disposed within a sample chamber 300. In some examples, the sample chamber 300 can be any chamber or passage that can receive the surfactant solution 302. For example, the sample chamber 300 can include an opening 304 for receiving the surfactant solution 302 or a channel 306 for allowing the surfactant solution 302 to circulate or flow within the sample chamber 300. In some examples, the surfactant solution 302 may be disposable within the sample chamber 300 in any manner, including without limitation, through manual disposal (e.g., manual labor) or through automated disposal (e.g., by an apparatus, device, machine, or the like).

In some examples, the surfactant solution 302 can be injected into an injection well associated with a production well to sweep hydrocarbon fluids from within the production well to a surface of the production well, which can improve recovery of the hydrocarbon fluids from within the production well. For example, the surfactant in the surfactant solution 302 can alter a wettability of the production well (e.g., a preference of a solid in the production well to contact a liquid or gas, such as, for example, hydrocarbon fluids in the production well) to improve recovery of hydrocarbon fluids. In some examples, the surfactant in the surfactant solution 302 can increase a mobility of hydrocarbon fluids in the production well and displace the hydrocarbon fluids from within the production well to the surface of the production well.

In block 508, the thin-layer substrate 200 is disposed within (e.g., positioned within or inserted into) the sample chamber 300. In some examples, a thin-layer chromatography device 116 can include the thin-layer substrate 200 and the sample chamber 300 and the thin-layer chromatography device 116 can be used to determine a type of surfactant solution 302 to be injected into an injection well associated with a production well to sweep hydrocarbon fluids from within the production well to a surface of the production well.

In block 510, a mobility index associated with the hydrocarbon fluid sample 202a is determined. In some examples, when the thin-layer substrate 200 is disposed within the sample chamber 300, the surfactant solution 302 can flow across the thin-layer substrate 200 and cover or travel a length 402 of the thin-layer substrate 200. The surfactant solution 302 may also contact the hydrocarbon fluid sample 202a as the surfactant solution 302 flows across the thin-layer substrate 200, which can cause the hydrocarbon fluid sample 202a to travel or flow from a first position on the thin-layer substrate 200 to a second position on the thin-layer substrate 200.

For example, the hydrocarbon fluid sample 202a can travel or flow from a first position near a first end 204 of the thin-layer substrate 200 to a second position on the thin-layer substrate 200 distal from the first end 204 (e.g., a second position near a second end 206 of the thin-layer substrate 200). In some examples, the hydrocarbon fluid sample 202a can travel a distance $D_a$ between the first position and the second position.

In some examples, the mobility index associated with the hydrocarbon fluid sample 202a can be determined based at least in part on the distance $D_a$ traveled by the hydrocarbon fluid sample 202a. For example, the mobility index can be based on a retention factor of the hydrocarbon fluid sample 202a. The retention factor can be ratio of the distance $D_a$ traveled by the hydrocarbon fluid sample 202a and the length 402 traveled by the surfactant solution 302 along the thin-layer substrate 200. As an example, the retention factor associated with the hydrocarbon fluid sample 202a can be determined based on the following formula:

$$R_f = \frac{\text{Distance traveled by hydrocarbon fluid sample}}{\text{distance traveled by surfactant solution}}$$

In the formula above, $R_f$ is the retention factor, distance traveled by hydrocarbon fluid sample is the distance $D_a$ and distance traveled by surfactant solution is the length 402 traveled by the surfactant solution 302.

In another example, the mobility index associated with the hydrocarbon fluid sample 202a can be determined based on a rate (e.g., a velocity) at which the hydrocarbon fluid sample 202a travels the distance $D_a$.

Figure 6:
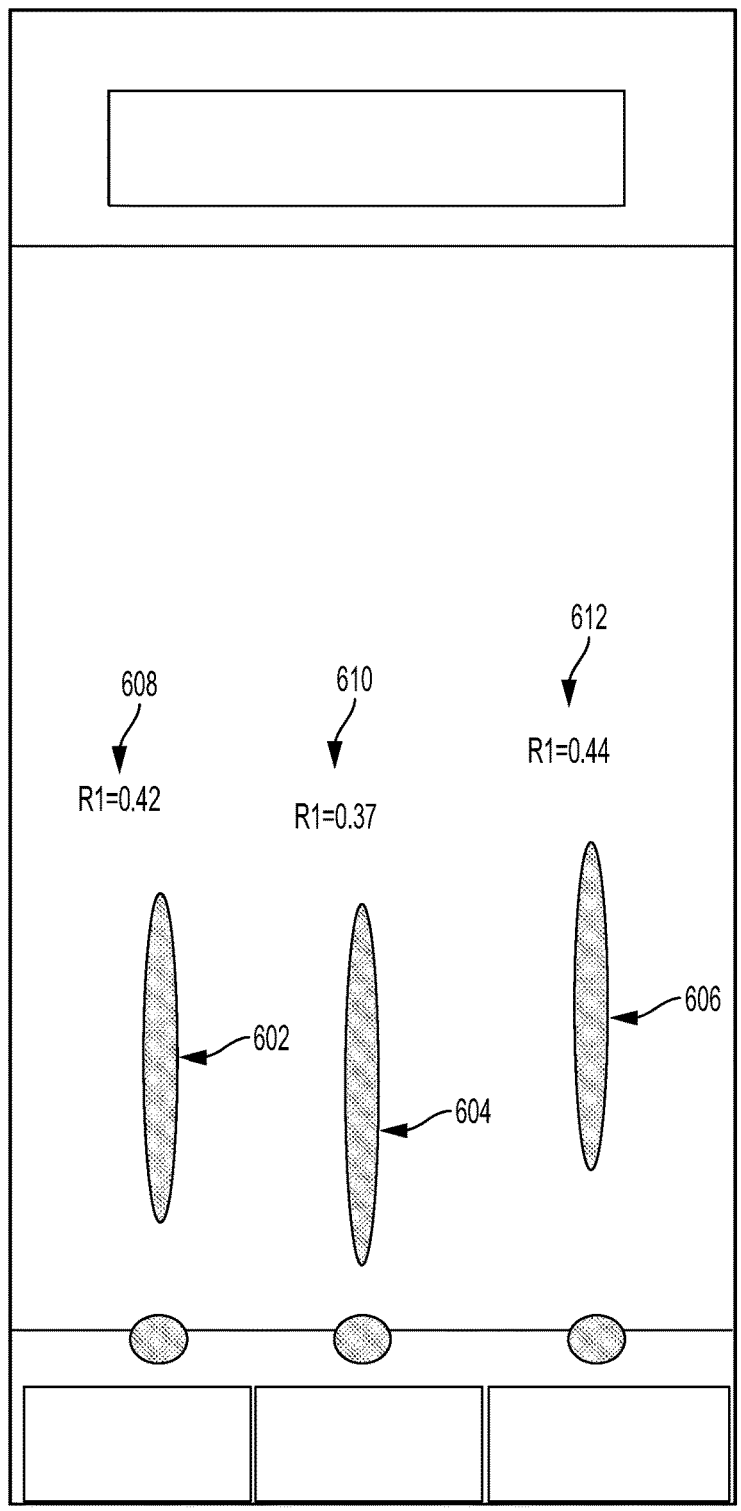
FIG. 6 is an image depicting mobility indices associated with various hydrocarbon fluid samples, according to one example of the present disclosure.

FIG. 6 is an image depicting mobility indices 608, 610, 612 associated with various hydrocarbon fluid samples 602, 604, 606, according to one example of the present disclosure. In this example, the various hydrocarbon fluid samples 602, 604, 606 can be disposed on a thin-layer substrate (e.g., the thin-layer substrate 200 of FIG. 2-4) and positioned within a sample chamber that includes a surfactant solution (e.g., the sample chamber 300 of FIG. 3). As depicted in FIG. 6, the mobility index 612 associated with hydrocarbon fluid sample 606 may be greater than the mobility indices 608, 610 associated with hydrocarbon fluid samples 602, 604, which may indicate that the surfactant solution included in the sample chamber may have a higher eluting capability with respect to hydrocarbon fluid sample 606 as compared to hydrocarbon fluid samples 602, 604.

Returning to block 510 of FIG. 5, in some examples, the adsorbent material on the thin-layer substrate 200 may affect the mobility index of the hydrocarbon fluid sample 202a. For example, the adsorbent material can bond to the hydrocarbon fluid sample 202a and reduce a distance $D_a$ that the hydrocarbon fluid sample 202a can travel (e.g., reduce the distance between a first position of the hydrocarbon fluid sample 202a on the thin-layer substrate 200 and a second position of the hydrocarbon fluid sample 202a on the thin-layer substrate 200). As another example, the adsorbent material can bond to the hydrocarbon fluid sample 202a, and reduce a rate at which the hydrocarbon fluid sample 202a travels the distance $D_a$ from the first position on the thin-layer substrate 200 to the second position on the thin-layer substrate 200. In some examples, an impact of the adsorbent material on the mobility index of the hydrocarbon fluid sample 202a can depend on various factors such as, for example, a type of the hydrocarbon fluid sample 202a or a type of the adsorbent material.

The surfactant in the surfactant solution 302 may also affect the mobility index of the hydrocarbon fluid sample 202a by reducing a surface tension or weakening a bond between the adsorbent material and the hydrocarbon fluid sample 202a. For example, reducing the surface tension or weakening the bond between the adsorbent material and the hydrocarbon fluid sample 202a can improve a mobility of the hydrocarbon fluid sample 202a along the thin-layer substrate 200 (e.g., an ability of the hydrocarbon fluid sample 202a to travel from the first position on the thin-layer substrate 200 to the second position on the thin-layer substrate 200). In some examples, improving the mobility of the hydrocarbon fluid sample 202a along the thin-layer substrate 200 can improve a mobility index associated with the hydrocarbon fluid sample 202a.

As an example, when the surfactant in the surfactant solution 302 contacts the hydrocarbon fluid sample 202a, the surfactant can reduce the surface tension between the adsorbent material and the hydrocarbon fluid sample 202a, which may increase a distance that the hydrocarbon fluid sample 202a can travel along the thin-layer substrate 200 (e.g., increasing the distance $D_a$). As another example, when the surfactant in the surfactant solution 302 contacts the hydrocarbon fluid sample 202a, the surfactant can reduce the surface tension between the adsorbent material and the hydrocarbon fluid sample 202a, which may increase a rate or velocity at which the hydrocarbon fluid sample 202a travels the distance $D_a$.

In some examples, a mobility index of the hydrocarbon fluid sample 202a when the hydrocarbon fluid sample 202a contacts the surfactant solution 302 or an impact of the surfactant solution 302 on the mobility index of the hydrocarbon fluid sample 202a can depend on various factors, such as, for example, a type of the adsorbent material on the thin-layer substrate 200, a type of fluid in the surfactant solution, and a type of surfactant in the surfactant solution 302.

In some examples, the mobility index associated with the hydrocarbon fluid sample 202a can indicate an eluting capability of the surfactant solution 302 with respect to the hydrocarbon fluid sample 202a. The eluting capability of the surfactant solution 302 can represent an ability of the surfactant solution 302 to displace or separate the hydrocarbon fluid sample 202a from the adsorbent material (e.g., an ability of the surfactant solution 302 to reduce a surface tension between the hydrocarbon fluid sample 202a and the adsorbent material or weaken a bond between the hydrocarbon fluid sample 202a and the adsorbent material).

In block 512, the surfactant solution is selected to be injected into a wellbore based at least in part on the mobility index associated with the hydrocarbon fluid sample 202a.

In some examples, a production well can include the hydrocarbon fluid sample 202a. The surfactant solution 302 can be selected to be injected into an injection well associated with the production well based on the mobility index of the hydrocarbon fluid sample 202a. For example, the mobility index associated with the hydrocarbon fluid sample 202a can be compared to the mobility index threshold value (e.g., a value of 0.5 or any suitable value) and the surfactant solution 302 may be selected to be injected into the injection well if the mobility index associated with the hydrocarbon fluid sample 202a is above the mobility index threshold. Injecting the surfactant solution 302 into the injection well if the mobility index associated with the hydrocarbon fluid sample 202a is above the mobility index threshold may improve hydrocarbon fluid recovery operations or other production operations. For example, injecting the surfactant solution 302 into the injection well may allow the surfactant in the surfactant solution 302 to displace the hydrocarbon fluid sample 202a or increase a mobility of the hydrocarbon fluid sample 202a within the production well and sweep the hydrocarbon fluid sample 202a from within the production well toward a surface of the production well.

In some examples, a mobility index associated with multiple hydrocarbon fluid samples 202a-d can be determined. A surfactant solution 302 can be selected to be injected into the injection well based on a comparison of the mobility indices associated with the hydrocarbon fluid samples 202a-d. For example, the mobility index associated with hydrocarbon fluid sample 202b may be greater than the mobility index associated with the hydrocarbon fluid sample 202a when the hydrocarbon fluid samples 202a-d contact the surfactant solution 302 in the sample chamber 300. Based on the comparison, the surfactant solution 302 can be selected to be injected into an injection well positioned proximate to a production well that includes hydrocarbon fluid sample 202b to increase a mobility of hydrocarbon fluid sample 202b and sweep the hydrocarbon fluid sample 202b from within the production well, which can enhance hydrocarbon fluid recovery.

In some examples, a mobility index associated with the hydrocarbon fluid sample 202a can be determined with respect to one or more types of surfactant solutions to determine a surfactant solution to be injected into an injection well to sweep hydrocarbon fluids from within a production well. For example, a sample chamber 300 of a thin-layer chromatography device 116 can include a first surfactant solution and a thin-layer substrate 200 that includes a hydrocarbon fluid sample 202a can be disposed within the first surfactant solution to determine a first mobility index associated with the hydrocarbon fluid sample 202a when the hydrocarbon fluid sample 202a contacts the first surfactant solution as described above. Subsequently, a second surfactant solution can be disposed within the sample chamber 300 after the thin-layer substrate 200 and the first surfactant solution are removed from the sample chamber 300. Another amount of the hydrocarbon fluid sample 202a can be disposed on the thin-layer substrate 200 (e.g., in block 504) and the thin-layer substrate 200, along with the hydrocarbon fluid sample 202a, can be inserted into the second surfactant solution to determine a second mobility index associated with the hydrocarbon fluid sample 202a when the hydrocarbon fluid sample 202a contacts the second surfactant solution. The first mobility index can be compared to the second mobility index to determine a surfactant solution to be injected into the injection well to sweep hydrocarbon fluids from within the production well. As an example, the production well can include the hydrocarbon fluid sample 202a and the second surfactant solution may be selected to be injected into the injection well if the second mobility index is greater than the first mobility index.

Thus, in some examples, the thin-layer chromatography device 116 can be used to select a particular surfactant solution 302 for a production well containing a particular hydrocarbon fluid sample 202a based on a mobility index associated with the hydrocarbon fluid sample 202a when the hydrocarbon fluid sample 202a contacts the surfactant solution 302 or an impact of the surfactant solution 302 on the mobility index of the hydrocarbon fluid sample 202a.

In some aspects, a thin-layer chromatography device for screening oil-field surfactants is provided according to one or more of the following examples:

Example #1

A method can include: disposing a layer of an adsorbent material on a substrate to form a thin-layer substrate; disposing a hydrocarbon fluid sample on a surface of the thin-layer substrate; disposing a surfactant solution within a sample chamber, the surfactant solution including a surfactant and a fluid; disposing the thin-layer substrate within the sample chamber; and determining a mobility index associated with the hydrocarbon fluid sample based on a distance traveled by the hydrocarbon fluid sample along the surface of the thin-layer substrate disposed within the sample chamber. The mobility index can indicate an eluting capability of the surfactant solution with respect to the hydrocarbon fluid sample and can be usable for selecting, from among a plurality of surfactant solutions, a particular surfactant solution for use in a wellbore associated with the hydrocarbon fluid sample, the particular surfactant solution including the surfactant solution.

Example #2

The method of Example #1 can include comparing the mobility index associated with the hydrocarbon fluid sample to a mobility index threshold and selecting the particular surfactant solution from among the plurality of surfactant solutions based on the mobility index being above the mobility index threshold.

Example #3

The method of any of Examples #1-2 can include: disposing a first surfactant solution within the sample chamber; disposing a first amount of the hydrocarbon fluid sample on the surface of the thin-layer substrate; disposing the thin-layer substrate that includes the first amount of the hydrocarbon fluid sample within the sample chamber and into the first surfactant solution; determining a first mobility index associated with the first amount of the hydrocarbon fluid sample based on a first distance traveled by the first amount of the hydrocarbon fluid sample along the surface of the thin-layer substrate disposed within the sample chamber, the first mobility index indicating an eluting capability of the first surfactant solution with respect to the hydrocarbon fluid sample; disposing a second surfactant solution within the sample chamber; disposing a second amount of the hydrocarbon fluid sample on the surface of the thin-layer substrate; disposing the thin-layer substrate that includes the second amount of the hydrocarbon fluid sample within the sample chamber and into the second surfactant solution; determining a second mobility index associated with the second amount of the hydrocarbon fluid sample based on a second distance traveled by the second amount of the hydrocarbon fluid sample along the surface of the thin-layer substrate disposed within the sample chamber, the second mobility index indicating an eluting capability of the second surfactant solution with respect to the hydrocarbon fluid sample; and comparing the first mobility index and the second mobility index for selecting the first surfactant solution or the second surfactant solution for use in the wellbore.

Example #4

The method of any of Examples #1-3 can include: disposing a plurality of hydrocarbon fluid samples on the surface of the thin-layer substrate; determining mobility indices associated with the hydrocarbon fluid samples; comparing mobility indices associated with the hydrocarbon fluid samples to determine a hydrocarbon fluid sample having a highest mobility index among the hydrocarbon fluid samples; and selecting the particular surfactant solution for use in a wellbore associated with the hydrocarbon fluid sample having the highest mobility index.

Example #5

The method of any of Examples #1-4 may feature the adsorbent material including at least one of silica, alumina, cellulose, sand, or a particle from within the wellbore.

Example #6

The method of any of Examples #1-5 may feature the surfactant solution including at least one of brine, produced water, or fracturing fluid.

Example #7

The method of any of Examples #1-6 may feature the substrate including glass, plastic, aluminum foil, or quartz.

Example #8

A device can include a sample chamber having an opening for receiving a surfactant solution that includes a surfactant and a fluid. The device can also include a thin-layer substrate disposable within the sample chamber. The thin-layer substrate can include a substrate and a layer of an adsorbent material disposed on the substrate on which an amount of a hydrocarbon fluid sample is disposable for determining a mobility index associated with the hydrocarbon fluid sample based on a distance traveled by the hydrocarbon fluid sample along a surface of the thin-layer substrate subsequent to the thin-layer substrate being positioned within the sample chamber containing the surfactant solution. The mobility index can indicate an eluting capability of the surfactant solution with respect to the hydrocarbon fluid sample.

Example #9

The device of Example #8 may feature the adsorbent material including at least one of silica, alumina, cellulose, sand, or a particle.

Example #10

The device of any of Examples #8-9 may feature the adsorbent material being collected from within a wellbore associated with the hydrocarbon fluid sample.

Example #11

The device of any of Examples #8-10 may feature the fluid including at least one of brine, produced water, or fracturing fluid.

Example #12

The device of any of Examples #8-11 may feature the substrate including glass, plastic, aluminum foil, or quartz.

Example #13

The device of any of Examples #8-12 may feature a plurality of hydrocarbon fluid samples being disposable on the thin-layer substrate for determining mobility indices associated with the plurality of hydrocarbon fluid samples. The mobility indices associated with the plurality of hydrocarbon fluid samples can be usable for selecting a particular surfactant solution for use in a wellbore associated with a hydrocarbon fluid sample having a highest mobility index among the plurality of hydrocarbon fluid samples.

Example #14

A device can include a thin-layer substrate. The thin-layer substrate can include a substrate and a layer of an adsorbent material disposed on the substrate on which a hydrocarbon fluid sample is disposable for determining a mobility index associated with the hydrocarbon fluid sample based on a distance traveled by the hydrocarbon fluid sample along a surface of the thin-layer substrate subsequent to the thin-layer substrate being positioned within a sample chamber containing a surfactant solution. The mobility index can indicate an eluting capability of the surfactant solution with respect to the hydrocarbon fluid sample.

Example #15

The device of Example #14 may feature the substrate including glass, plastic, aluminum foil, or quartz.

Example #16

The device of any of Examples #14-15 may feature the adsorbent material including at least one of silica, alumina, cellulose, or formation material.

Example #17

The device of any of Examples #14-16 may feature the adsorbent material being collected from within a wellbore.

Example #18

The device of any of Examples #14-17 may feature the surfactant solution including a surfactant and a fluid.

Example #19

The device of any of Examples #14-18 may feature the fluid including at least one of brine, produced water, or fracturing fluid.

Example #20

The device of any of Examples #14-19 may feature the hydrocarbon fluid samples being disposable on the thin-layer substrate for determining mobility indices associated with the hydrocarbon fluid samples, the mobility indices usable for selecting, from among a plurality of surfactant solutions, a particular surfactant solution for use in a wellbore associated with a hydrocarbon fluid sample having a highest mobility index among the hydrocarbon fluid samples, the particular surfactant solution including the surfactant solution in the sample chamber.

The foregoing description of certain examples, including illustrated examples, has been presented only for the purpose of illustration and description and is not intended to be exhaustive or to limit the disclosure to the precise forms disclosed. Numerous modifications, adaptations, and uses thereof will be apparent to those skilled in the art without departing from the scope of the disclosure.

What is claimed is:

1. A method comprising:
  disposing a layer of an adsorbent material on a substrate to form a thin-layer substrate;
  disposing a hydrocarbon fluid sample on a surface of the thin-layer substrate;
  disposing a surfactant solution within a sample chamber, the surfactant solution comprising a surfactant and a fluid;
  disposing the thin-layer substrate within the sample chamber;
  determining a mobility index associated with the hydrocarbon fluid sample based on a distance traveled by the hydrocarbon fluid sample along the surface of the thin-layer substrate disposed within the sample chamber, the mobility index indicating an eluting capability of the surfactant solution with respect to the hydrocarbon fluid sample and usable for selecting, from among a plurality of surfactant solutions, a particular surfactant solution for use in a wellbore associated with the hydrocarbon fluid sample, the particular surfactant solution comprising the surfactant solution;
  comparing the mobility index associated with the hydrocarbon fluid sample to a mobility index threshold;
  selecting the particular surfactant solution from among the plurality of surfactant solutions based on comparing the mobility index to the mobility index threshold; and
  injecting the particular surfactant solution into the wellbore to sweep hydrocarbon fluid from the wellbore.

2. The method of claim 1, further comprising:
  disposing a first surfactant solution within the sample chamber;
  disposing a first amount of the hydrocarbon fluid sample on the surface of the thin-layer substrate;
  disposing the thin-layer substrate that includes the first amount of the hydrocarbon fluid sample within the sample chamber and into the first surfactant solution;
  determining a first mobility index associated with the first amount of the hydrocarbon fluid sample based on a first distance traveled by the first amount of the hydrocarbon fluid sample along the surface of the thin-layer substrate disposed within the sample chamber, the first mobility index indicating an eluting capability of the first surfactant solution with respect to the hydrocarbon fluid sample;
  disposing, after removing the first surfactant solution from the sample chamber, a second surfactant solution within the sample chamber;
  disposing a second amount of the hydrocarbon fluid sample on the surface of the thin-layer substrate;
  disposing the thin-layer substrate that includes the second amount of the hydrocarbon fluid sample within the sample chamber and into the second surfactant solution;
  determining a second mobility index associated with the second amount of the hydrocarbon fluid sample based on a second distance traveled by the second amount of the hydrocarbon fluid sample along the surface of the thin-layer substrate disposed within the sample chamber, the second mobility index indicating an eluting capability of the second surfactant solution with respect to the hydrocarbon fluid sample; and
  comparing the first mobility index and the second mobility index for selecting the first surfactant solution or the second surfactant solution for use in the wellbore.

3. The method of claim 1, further comprising:
  disposing a plurality of hydrocarbon fluid samples on the surface of the thin-layer substrate;
  determining mobility indices associated with the hydrocarbon fluid samples;
  comparing mobility indices associated with the hydrocarbon fluid samples to determine a hydrocarbon fluid sample having a highest mobility index among the hydrocarbon fluid samples; and
  selecting the particular surfactant solution for use in a wellbore associated with the hydrocarbon fluid sample having the highest mobility index.

4. The method of claim 1, wherein the adsorbent material includes at least one of silica, alumina, cellulose, sand, or a particle from within the wellbore.

5. The method of claim 1, wherein the surfactant solution further comprises at least one of brine, produced water, or fracturing fluid.

6. The method of claim 1, wherein the substrate comprises glass, plastic, aluminum foil, or quartz.

7. A system comprising:
 a sample chamber having an opening for receiving a surfactant solution that includes a surfactant and a fluid; and
 a thin-layer substrate disposable within the sample chamber, the thin-layer substrate comprising a substrate and a layer of an adsorbent material disposed on the substrate on which an amount of a hydrocarbon fluid sample from within a wellbore is disposable for determining a mobility index associated with the hydrocarbon fluid sample based on a distance traveled by the hydrocarbon fluid sample along a surface of the thin-layer substrate subsequent to the thin-layer substrate being positioned within the sample chamber containing the surfactant solution, the mobility index indicating an eluting capability of the surfactant solution with respect to the hydrocarbon fluid sample,
 wherein the surfactant solution is selectable from a plurality of surfactant solutions and each surfactant solution of the plurality of surfactant solutions is injectable into the wellbore to sweep hydrocarbon fluid from the wellbore based on differing values of the mobility index of the hydrocarbon fluid relative to a mobility index threshold.

8. The system of claim 7, wherein the adsorbent material includes at least one of silica, alumina, cellulose, sand, or a particle.

9. The system of claim 8, wherein the adsorbent material is collected from within a wellbore associated with the hydrocarbon fluid sample.

10. The system of claim 7, wherein the fluid includes at least one of brine, produced water, or fracturing fluid.

11. The system of claim 7, wherein the substrate comprises glass, plastic, aluminum foil, or quartz.

12. The system of claim 7, wherein a plurality of hydrocarbon fluid samples are disposable on the thin-layer substrate for determining mobility indices associated with the plurality of hydrocarbon fluid samples, the mobility indices usable for selecting a particular surfactant solution for use in a wellbore associated with the hydrocarbon fluid sample having a highest mobility index among the plurality of hydrocarbon fluid samples.

13. A system comprising:
 a thin-layer substrate comprising:
 a substrate; and
 a layer of an adsorbent material disposed on the substrate on which a hydrocarbon fluid sample obtained from within a wellbore is disposable for determining a mobility index associated with the hydrocarbon fluid sample based on a distance traveled by the hydrocarbon fluid sample along a surface of the thin-layer substrate subsequent to the thin-layer substrate being positioned within a sample chamber containing a surfactant solution, the mobility index indicating an eluting capability of the surfactant solution with respect to the hydrocarbon fluid sample,
 wherein the surfactant solution is selectable from a plurality of additional surfactant solutions and each surfactant solution of the plurality of surfactant solutions is injectable into the wellbore to sweep hydrocarbon fluid from the wellbore based on differing values of the mobility index of the hydrocarbon fluid relative to a mobility index threshold.

14. The system of claim 13, wherein the substrate comprises glass, plastic, aluminum foil, or quartz.

15. The system of claim 13, wherein the adsorbent material includes at least one of silica, alumina, cellulose, or formation material.

16. The system of claim 15, wherein the adsorbent material is collected from within the wellbore.

17. The system of claim 13, wherein the surfactant solution comprises a surfactant and a fluid.

18. The system of claim 17, wherein the fluid comprises at least one of brine, produced water, or fracturing fluid.

19. The system of claim 13, wherein hydrocarbon fluid samples are disposable on the thin-layer substrate for determining mobility indices associated with the hydrocarbon fluid samples, the mobility indices usable for selecting, from among the plurality of additional surfactant solutions, a particular surfactant solution for use in a wellbore associated with the hydrocarbon fluid sample having a highest mobility index among the hydrocarbon fluid samples, the particular surfactant solution including the surfactant solution in the sample chamber.

\* \* \* \* \*